(12) United States Patent
Downer

(10) Patent No.: US 9,226,819 B2
(45) Date of Patent: Jan. 5, 2016

(54) INTRAOCULAR LENS DELIVERY DEVICE WITH A MULTI-PART PLUNGER TIP

(71) Applicant: Alcon Research, Ltd., Fort Worth, TX (US)

(72) Inventor: David A. Downer, Fort Worth, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 267 days.

(21) Appl. No.: 13/961,287

(22) Filed: Aug. 7, 2013

(65) Prior Publication Data
US 2013/0317514 A1 Nov. 28, 2013

Related U.S. Application Data

(63) Continuation of application No. 12/615,527, filed on Nov. 10, 2009, now abandoned.

(60) Provisional application No. 61/113,627, filed on Nov. 12, 2008.

(51) Int. Cl.
*A61F 2/16* (2006.01)

(52) U.S. Cl.
CPC ............... *A61F 2/167* (2013.01); *A61F 2/1678* (2013.01)

(58) Field of Classification Search
CPC ...... A61F 2/167; A61F 2/1672; A61F 2/1678
See application file for complete search history.

(56) References Cited

U.S. PATENT DOCUMENTS

| 4,615,701 | A | 10/1986 | Woods |
| 4,681,102 | A | 7/1987 | Bartell |
| 4,919,130 | A | 4/1990 | Stoy et al. |
| 5,275,604 | A | 1/1994 | Rheinish et al. |
| 5,494,484 | A | 2/1996 | Feingold |
| 5,496,328 | A | 3/1996 | Nakajima et al. |
| 5,499,987 | A | 3/1996 | Feingold |
| 5,616,148 | A | 4/1997 | Eagles et al. |
| 5,620,450 | A | 4/1997 | Eagles et al. |
| 5,653,715 | A | 8/1997 | Reich et al. |
| 5,947,976 | A | 9/1999 | Van Noy et al. |
| 6,162,229 | A | 12/2000 | Feingold et al. |
| 6,398,789 | B1 | 6/2002 | Capetan |
| 6,558,395 | B2 | 5/2003 | Hjertman et al. |
| 6,592,591 | B2 | 7/2003 | Polla et al. |
| 6,923,815 | B2 | 8/2005 | Brady et al. |

(Continued)

FOREIGN PATENT DOCUMENTS

| EP | 1 849 436 | 10/2007 |
| EP | 1 360 946 | 2/2008 |

(Continued)

OTHER PUBLICATIONS

PCT International Search Report for corresponding PCT/US2009/063805 with mailing date Feb. 19, 2010.
PCT International Written Opinion for corresponding PCT/US2009/063805 with mailing date Feb. 19, 2010.

*Primary Examiner* — Sarah W Aleman
(74) *Attorney, Agent, or Firm* — Scott A. Chapple

(57) ABSTRACT

The present invention is directed to the provision of an intraocular lens delivery device having a plunger with a multi-part plunger tip. The plunger tip includes a first part and a second part wherein the first part releases from the second part during travel of the plunger through the body of a delivery cartridge.

16 Claims, 3 Drawing Sheets

(56) References Cited

U.S. PATENT DOCUMENTS

| | | |
|---|---|---|
| 7,033,366 B2 | 4/2006 | Brady |
| 7,131,976 B2 * | 11/2006 | Kobayashi et al. ........... 606/107 |
| 7,156,852 B2 | 1/2007 | Dye et al. |
| 7,156,854 B2 | 1/2007 | Brown et al. |
| 2005/0149057 A1 | 7/2005 | Rathert |
| 2007/0005135 A1 * | 1/2007 | Makker et al. ............... 623/6.12 |
| 2008/0058830 A1 | 3/2008 | Cole et al. |
| 2009/0131953 A1 | 5/2009 | Quintin et al. |

FOREIGN PATENT DOCUMENTS

| | | |
|---|---|---|
| WO | 97/26841 | 7/1997 |
| WO | 00/40175 | 7/2000 |
| WO | 2005/065589 | 7/2005 |
| WO | 2006059183 | 6/2006 |
| WO | 2006/077349 | 7/2006 |

* cited by examiner

INTRAOCULAR LENS DELIVERY DEVICE WITH A MULTI-PART PLUNGER TIP

CROSS REFERENCE TO RELATED APPLICATION

This application is a continuation of patent application Ser. No. 12/615,527 filed Nov. 10, 2009, which; claims priority under 35 U.S.C. §119 to U.S. Provisional Patent Application No. 61/113,627, filed Nov. 12, 2008, the entire contents of which are incorporated herein by reference.

TECHNICAL FIELD OF THE INVENTION

The present invention relates to an intraocular lens delivery device with a multi-part plunger tip. More particularly, the present invention relates to an intraocular lens delivery device that includes a plunger tip with a first part and a second part wherein the first part releases from the second part during travel of the plunger through the body of a delivery cartridge.

BACKGROUND OF THE INVENTION

The human eye functions to provide vision by transmitting and refracting light through a clear outer portion called the cornea, and further focusing the image by way of a lens onto the retina at the back of the eye. The quality of the focused image depends on many factors including the size, shape and length of the eye, and the shape and transparency of the cornea and lens.

When trauma, age, disease or other malady cause an individual's natural crystalline lens to become less transparent, vision deteriorates because of the diminished light which can be transmitted to the retina. This deficiency in the lens of the eye is often referred to as a cataract. The treatment for this condition is surgical removal of the natural crystalline lens and implantation of an intraocular lens (IOL).

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. One commonly used injector cartridge design is illustrated in U.S. Pat. No. 4,681,102 (Bartell), and includes a split, longitudinally hinged cartridge. Other designs are illustrated in U.S. Patent Nos. 5,494,484 and 5,499,987 (Feingold) and U.S. Pat. Nos. 5,616,148 and 5,620,450 (Eagles, et al.), the entire contents of which are incorporated herein by reference. Still other cartridges are described in U.S. Pat. No. 5,275,604 (Rheinish, et al.), U.S. Pat. No. 5,653,715 (Reich, et al.) and U.S. Pat. No. 5,947,876 (Van Noy, et al.), the entire contents of which are incorporated herein by reference.

At least a portion of the lumen of the cartridge typically becomes progressively smaller (i.e., smaller in cross-sectional area) closer to the nozzle or exit point of the cartridge and the IOL typically becomes rolled, folded and/or compressed as it travels along this portion of the lumen. To foster the movement of the IOL along the lumen, it is generally desirable for the tip of plunger to substantially fill the cross-sectional area of the lumen as the plunger is moved along the length of the lumen. By substantially filling the cross-sectional area, the plunger tip helps ensure that an IOL is reliably pushed along the lumen without a portion of the IOL becoming undesirably trapped between the plunger tip and the cartridge.

To allow the plunger tip to move along the progressively smaller cross-sectional area while continuing to substantially fill the cross-sectional area of the lumen, the plunger tip would traditionally be formed of a soft compressible material that is compressed as it travels along the lumen. This approach can be problematic however. The amount of compression of the plunger tip can become undesirably high particularly toward the nozzle of the cartridge where the cross-sectional area of the lumen can become quite small. In turn, such compression can cause undesirable resistance to travel of the plunger along the lumen as well as other undesirable effects.

Thus, it would be quite desirable to provide an intraocular lens delivery device having a plunger that includes a plunger tip wherein the plunger tip can compress as it moves along a lumen that is becoming progressively smaller and wherein the plunger tip avoids the development of undesirably high forces associated with conventional soft tips.

SUMMARY OF THE INVENTION

Accordingly, the present invention is directed to an IOL delivery device that includes a delivery cartridge and a plunger having a plunger tip. The delivery cartridge includes an internal surface defining a lumen extending along the cartridge. At least a portion of the lumen has a cross-sectional area that becomes progressively smaller as the cross-sectional area is taken at locations progressively closer to the nozzle. The plunger tip is being defined by an internal member, an external member and an intermediate member, the external member being formed of a relatively compressible material and the intermediate member being formed of a relatively non-compressible material. During delivery of an IOL, the plunger tip travels along the at least a portion of the lumen causing the external member to compress a substantial amount while the intermediate member remains substantially non-compressed. Upon achieving the substantial amount of compression, the internal member releases from the intermediate member and continues the delivery of the IOL.

The external member is formed of a material typically having an elongation at break that is at least 350%, more typically at least 800%, still more typically at least 1500%. The intermediate member is formed of a material typically having an elongation at break that is no greater than 300%, more typically no greater than 100%, still more typically no greater than 50%. Moreover, the material forming the external member has an elongation at break that is at least 2×, more typically at least 4× and still more typically at least 8× an elongation at break of the material forming the intermediate member. The internal member can be an end portion of a shaft of the plunger. Further, it is contemplated that the delivery cartridge can include a stop feature that stops the travel of the external member after substantial amount of compression of the external member.

DETAILED DESCRIPTION OF THE INVENTION

The present invention is predicated upon the provision of an IOL delivery device that includes a delivery cartridge and a plunger having a multi-part plunger delivery tip. The delivery tip includes a relatively compressible member, a relatively incompressible member and an internal member. The delivery cartridge defines a lumen having a cross-sectional area that becomes progressively smaller as the cross-sectional area is taken closer to a nozzle of the cartridge. During delivery of an IOL, the compressible member of the plunger tip member undergoes substantial compression as the plunger tip travels along the progressively smaller cross-sectional area. During such compression, the relatively incompressible member shields the internal member from being substantially compressed by or lodged within the external member. The internal member of the plunger tip is then released from the relatively compressible member, the relatively incompressible member or both and completes the delivery of the IOL.

Figure 1:
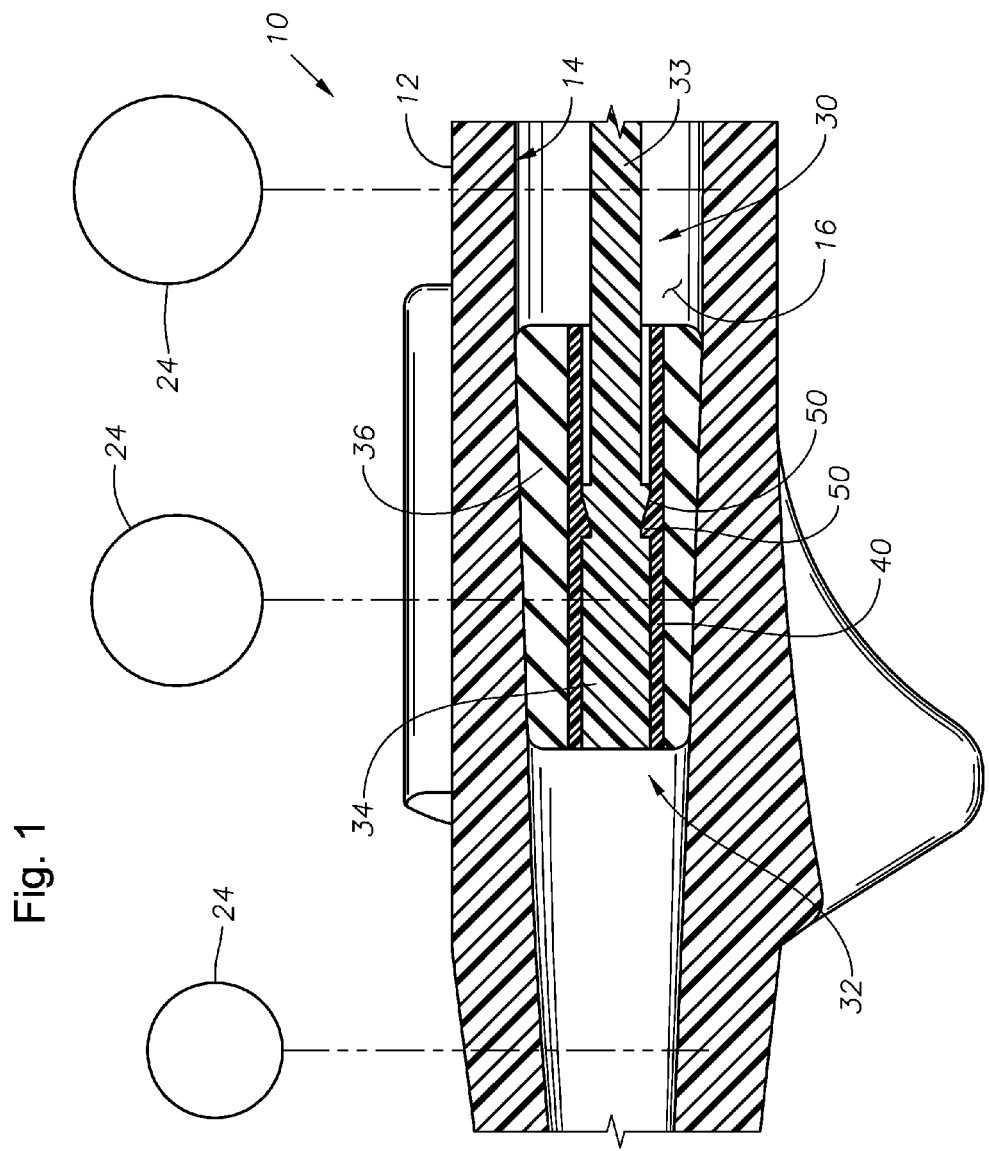
FIG. 1 is a sectional view of a portion of an exemplary IOL delivery device according to an aspect of the present invention.
Figure 2:
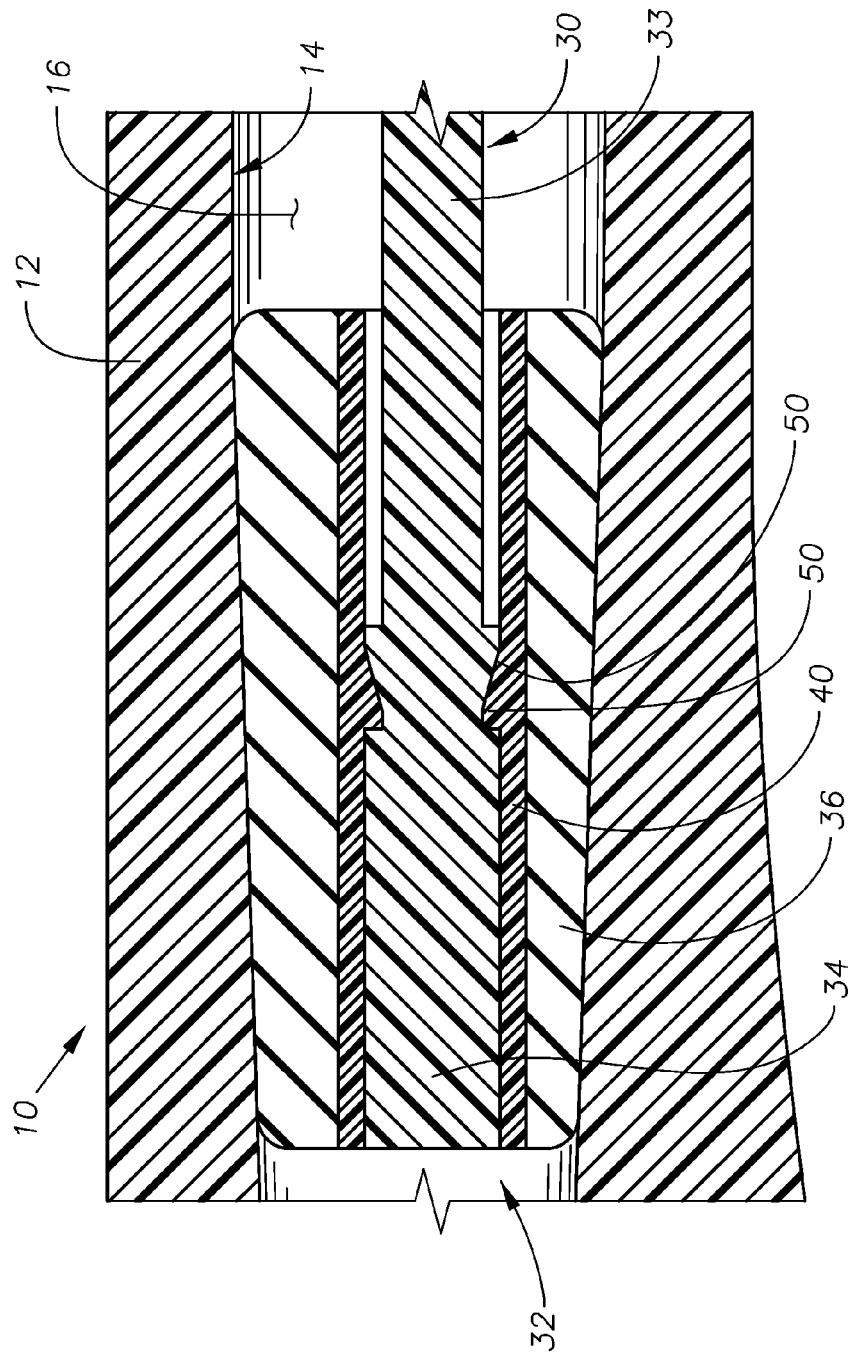
FIG. 2 is another sectional view of a portion of the exemplary IOL delivery device shown in FIG. 1.
Figure 3:
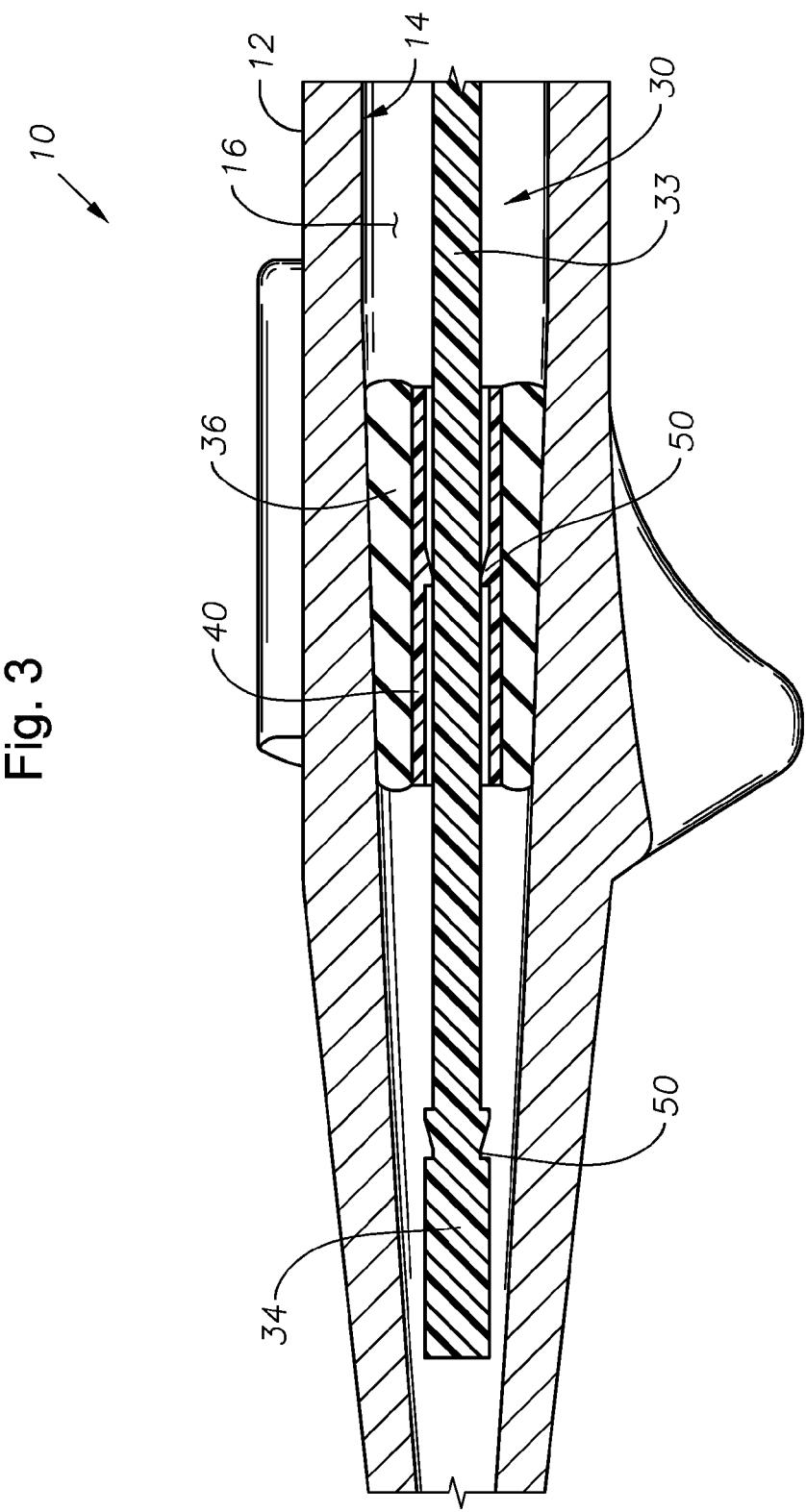
FIG. 3 is another sectional view of a portion of the exemplary IOL delivery device shown in FIG. 1.

With reference to FIGS. 1-3, there is illustrated an exemplary IOL delivery device 10 according to the present invention. The device 10 includes a delivery cartridge 12 having an internal surface 14 defining a lumen 16 extending along the cartridge 12. The illustrated lumen 16 extends along a length (L) of the cartridge 12. As can be seen, a cross sectional area 24 of the lumen 16 becomes progressively smaller along at least a portion of the lumen 16 as the cross-sectional area 24 is taken at locations progressively closer to a nozzle (not shown) of the cartridge 12.

The device 10 includes a plunger 30 having an elongated member 32 and a plunger tip 32 at a distal end of the elongated member 32. The plunger tip 32 is defined by an internal member 34, an external relatively compressible member 36 and an intermediate relatively incompressible member 40.

In the embodiment shown, the internal member 34 is a portion of the elongated member 32. Also as shown, the internal member 34 is integrally formed of the same material and as a singular part with the elongated member 33. However, it is contemplated that the internal member 34 may be a separate part formed of a separate material and attached to the elongated member 32 directly or through one or more other components.

The internal member 34 and hence the elongated member 33 may be formed of variety of materials such as metals or polymeric materials. In a preferred embodiment, the internal member is formed of a relatively rigid polymeric material. Exemplary potential polymeric materials include, without limitation, polystyrenes, polypropylenes, polycarbonates, combinations thereof or the like. It is also contemplated that the internal member 34 may itself include its own tip (not shown), which would typically be formed of material that is softer or more compressible than the material of the internal member 34.

The intermediate member 40 can also be formed of a variety of materials such as metal or polymeric materials as long as the material is relatively rigid as compared to the material that forms the external member 36. The material forming the intermediate member 40 is preferably a polymeric material and, like the internal member 34, suitable materials can include, without limitation, polystyrenes, polypropylenes, polycarbonates, polyetherimides, polyethylether ketones, polyether ether ketones, styrenics (e.g., acrylonitrile butadiene styrene), combinations thereof or the like. Preferably, the material forming the intermediate member 40 has a an elongation at break that is no greater than 300%, more typically no greater than 100%, still more typically no greater than 50%.

Elongation at break, as used herein, can be determined in accordance with ASTM D412.

As suggested, the material forming the external member 36 is relatively soft and compressible relative to the material forming the intermediate member 40. The material forming the external member is also preferably a polymeric material and will typically be entirely or substantially entirely an elastomer (e.g., a thermoset or thermoplastic elastomer). Examples of suitable materials include, without limitation, polyurethanes, butadiene rubbers, styrenic block copolymers, polyolefin blends such as ethylene propylene diene monomer elastomers, thermoplastic copolyesters, thermoplastic polyamides, polyurethanes, combinations thereof or the like. Preferably, the material forming the external member 36 has an elongation at break that is at least 350%, more typically at least 800% and still more typically at least 1500%. It is also preferable that the material of the external member 36 has an elongation at break that is at least 2×, more typically at least 4× and still more typically at least 8× an elongation at break of the material forming the intermediate member 40. As used herein, 2×, 4× and 8× respectively means two times, four times and eight times and as applied to an elongations of 100% would respectively mean 200%, 400% and 800%.

Again with reference to FIGS. 1-3, the illustrated exemplary external member 36 is annular in shape and extends about and/or substantially or entirely surrounds and encircles the intermediate member 40, the internal member 34 or both. The illustrated exemplary intermediate member 40 is also annular in shape and extends about and/or substantially or entirely surrounds and encircles the internal member 34. Of course, the skilled artisan will be able to contemplate other arrangements of these members within the scope of the present invention.

The internal member 34, the external member 36, the intermediate member 40 or a combination thereof typically includes one or more retention features 50 for releasably maintaining the intermediate member 40, the external member 36 or both in the same position relative to the internal member 34. In the illustrated embodiment the retention features 50 include a protrusion extending from the intermediate member 40 and a cavity disposed in the internal member 34, the cavity receiving the protrusion for maintaining the aforementioned relative position. Of course, the skilled artisan will be able to contemplate multiple other retention feature configurations within the scope of the present invention.

During delivery of an IOL, an individual or machine pushes the plunger 30 causing the plunger tip 32 to travel along the lumen 16. At some point, the plunger tip 32 travels along at least the portion of the lumen 16 having the progressively smaller cross-sectional area 24. In turn, this causes the external member 36 to compress a substantial amount while the intermediate member 40 remains substantially non-compressed. As used herein, a substantial amount of compression includes a movement of an outer surface of the external member to a distance at least 10%, more typically at least 20% and even more typically at least 30% closer to the intermediate member 40. For exemplary purposes, 10% closer means 10% of the original distance or, more particularly, for a surface that is 10 millimeters (mm) away, 10% closer means 9 mm away.

Upon achieving the substantial amount of compression of the external member 36, the retention features 50 release the internal member 34 from the intermediate member 40. The internal member 34 then extends out away from the external member 36, the intermediate member 40 or both and continues to push the IOL to continue the delivery of the IOL typically all of the way out through the nozzle of the cartridge 12.

In the embodiment shown, the external member 36 is gradually compressed until enough force is built up against the retention features 50, causing the retention features 50 to release the internal member 34 from the intermediate and external members 40, 36. However, it is to be understood that the cartridge 12 could include a stop (not shown) that the external member 36 or intermediate member 40 or both contact thereby causing stoppage of travel of the external member 36 and intermediate member 40 and release of the internal member 34 after substantial compression of the external member 36. For example, and without limitation, the internal lumen 16 could include a portion of rapidly decreasing cross-sectional area or the cartridge 12 could include a protrusion that would quickly stop travel of the external member 36 and intermediate member 40.

Advantageously, the plunger tip of the present invention provides a relatively large surface area for pushing an IOL prior to release of the internal member. Moreover, that surface area conforms to the lumen through which it travels at least until the internal member releases from the intermediate and external members. Upon such release, the IOL is sufficiently folded and/or compressed such that the internal member provides sufficient surface area to continue the advancement of the IOL. In this manner, the IOL can be reliably delivered without frictional and/or compressive forces generated by the tip becoming undesirably high.

It is contemplated that multiple different IOL delivery systems can be modified to include the lumen and plunger of the present invention. Example of such systems are disclosed in, without limitation, U.S. Pat. Nos. 4,615,701; 6,398,789; 6,592,591; 7,033,366; 7,156,852; and 7,156,854, all of which are incorporated herein by reference for all purposes.

The entire contents of all cited references in this disclosure are specifically incorporated herein by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

I claim:

1. A method of delivering an IOL to an eye, the method comprising:
providing a delivery cartridge having an internal surface defining a lumen extending along the cartridge wherein at least a portion of the lumen has a cross-sectional area that becomes progressively smaller as the cross-sectional area is taken at locations progressively closer to a nozzle of the cartridge;
providing an IOL disposed within the cartridge; and
providing a plunger having a plunger tip that travels along the lumen of the cartridge, the plunger tip being defined by an internal member, an external member and an intermediate member, the external member being formed of a first material having an elongation at break that is at least 350% and the intermediate member being formed of a second material having an elongation at break that is no greater than 300%;
causing the plunger tip to travel along the at least a portion of the lumen such that the external member compresses a substantial amount while causing the IOL to fold and compress and while the intermediate member remains substantially non-compressed wherein the substantial amount of compression includes a movement of an outer surface of the external member to a distance at least 10% closer to the intermediate member; and
upon achieving the substantial amount of compression, causing the internal member to release from the intermediate member and continue the delivery of the IOL.

2. A method as in claim 1 wherein the substantial amount of compression includes a movement of the outer surface of the external member to a distance at least 30% closer to the intermediate member.

3. A method as in claim 1 wherein the external member is formed of a material having an elongation at break that is at least 800%.

4. A method as in claim 1 wherein the intermediate member is formed of a material having an elongation at break that is no greater than 50%.

5. A method as in claim 1 wherein the intermediate member is formed of a material having an elongation at break that is no greater than 100%.

6. A method as in claim 1 wherein the external member is formed of a first material, the intermediate member is formed of second material and the first material has an elongation at break that is at least two times an elongation at break of the second material.

7. A method as in claim 1 wherein the external member is formed of a first material, the intermediate member is formed of second material and the first material has an elongation at break that is at least four times an elongation at break of the second material.

8. A method as in claim 1 wherein the internal member is an end portion of a shaft of the plunger.

9. A method as in claim 1 wherein the material that forms the external member includes a substantial portion of elastomer.

10. A method as in claim 9 wherein the external member includes at least 30% by weight elastomer.

11. A method as in claim 9 wherein the external member includes at least 50% by weight elastomer.

12. A method of delivering an IOL to an eye, the method comprising:
providing a delivery cartridge having an internal surface defining a lumen extending along the cartridge wherein at least a portion of the lumen has a cross-sectional area that becomes progressively smaller as the cross-sectional area is taken at locations progressively closer to a nozzle of the cartridge;
providing an IOL disposed within the cartridge; and
providing a plunger having a plunger tip that travels along the lumen of the cartridge, the plunger tip being defined by an internal member, an external member and an intermediate member, the external member being formed of a first material having an elongation at break that is at least 350% and the intermediate member being formed of a second material having an elongation at break that is no greater than 100%;

causing the plunger tip to travel along the at least a portion of the lumen such that the external member compresses a substantial amount while causing the IOL to fold and compress and while the intermediate member remains substantially non-compressed wherein the substantial amount of compression includes a movement of an outer surface of the external member to a distance at least 20% closer to the intermediate member; and upon achieving the substantial amount of compression, causing the internal member to release from the intermediate member and continue the delivery of the IOL wherein the internal member, the external member, the intermediate member or a combination thereof includes one or more retention features for releasably maintaining the intermediate member the external member or both in the same position relative to the internal member until the internal member releases from the intermediate member.

13. A method as in claim 12 wherein the external member is formed of a material having an elongation at break that is at least 800%.

14. A method as in claim 12 wherein the intermediate member is formed of a material having an elongation at break that is no greater than 50%.

15. A method as in claim 12 wherein the external member is formed of a first material, the intermediate member is formed of second material and the first material has an elongation at break that is at least four times an elongation at break of the second material.

16. A method as in claim 12 wherein the external member includes at least 30% by weight elastomer.

* * * * *